United States Patent [19]

Winkelmann et al.

[11] 4,042,705

[45] * Aug. 16, 1977

[54] 1-METHYL-2-(PHENYL-OXYMETHYL)-5-NITRO-IMIDAZOLES AND PROCESS FOR THEIR MANUFACTURE

[75] Inventors: Erhardt Winkelmann, Kelkheim, Taunus; Wolfgang Raether, Dreieichenhain, both of Germany

[73] Assignee: Hoechst Aktiengesellschaft, Frankfurt am Main, Germany

[ * ] Notice: The portion of the term of this patent subsequent to June 2, 1994, has been disclaimed.

[21] Appl. No.: 704,100

[22] Filed: July 9, 1976

[30] Foreign Application Priority Data

July 12, 1975 Germany .............................. 2531303
Feb. 11, 1976 Germany .............................. 2605222

[51] Int. Cl.$^2$ ................. C07D 233/94; A61K 31/415
[52] U.S. Cl. ................................... 424/273 R; 548/339
[58] Field of Search ......................... 260/309; 424/273

[56] References Cited

U.S. PATENT DOCUMENTS

| | | | |
|---|---|---|---|
| 3,682,951 | 8/1972 | Kreider | 260/309 |
| 3,714,179 | 1/1973 | Tweit | 260/309 |
| 3,796,704 | 3/1974 | Metzger et al. | 260/309 |
| 3,828,065 | 8/1974 | Kreider | 260/309 |
| 3,842,097 | 10/1974 | Tweit | 260/309 |
| 3,910,925 | 10/1975 | Kreider | 260/309 |
| 3,922,277 | 11/1975 | Winkelmann et al. | 260/309 |

FOREIGN PATENT DOCUMENTS

2,124,103  11/1971  Germany .............................. 260/309

OTHER PUBLICATIONS

Freiter et al. J. Heterocyclic Chem. 1973, vol. 10, pp. 391-394.
Hoff et al. I Chem. Abst. 1972, vol. 76, No. 72513m.
Hoff et al. II Chem. Abst. 1972, vol. 76, No. 140811j.
Hoffer Chem. Abst. 1968, vol. 68, No. 105198c.
Swett et al., J. Med. Chem., 1970, vol. 13, pp. 968-970.
Tweit, Chem. Abst., 1974, vol. 81, No. 120630z.

*Primary Examiner*—Natalie Trousof
*Attorney, Agent, or Firm*—Curtis, Morris & Safford

[57] ABSTRACT

1-Methyl-2-(phenyl-oxymethyl)-5-nitro-imidazoles and a process for preparing them are disclosed. The compounds of the invention are suitable for the treatment of protozoal diseases caused in humans and animals and of bacteria and fungi.

3 Claims, No Drawings

1-METHYL-2-(PHENYL-OXYMETHYL)-5-NITRO-IMIDAZOLES AND PROCESS FOR THEIR MANUFACTURE

The present invention relates to 1-methyl-2-(phenyl-oxymethyl)-5-nitro-imidazoles and to a process for their manufacture.

1-(2-hydroxyethyl)-2-methyl-5-nitro-imidazole (Metronidazol) is being used for the treatment of protozoal diseases, such as trichomoniasis and amoebiasis.

Object of this invention are 1-methyl-2-(phenyl-oxymethyl)-5-nitro-imidazoles of the formula I

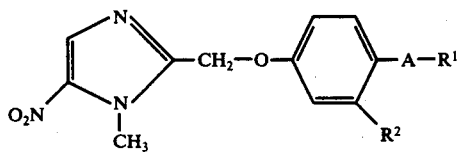

(I)

in which A stands for a sulfur atom or a sulfoxide (—SO—) group, $R^1$ stands for methyl or ethyl, and $R^2$ for hydrogen, methyl or halogen.

Further object of this invention is a process for the manufacture of 1-methyl-2-(phenyl-oxymethyl)-5-nitro-imidazoles of the formula I, which comprises
a. reacting a nitro-imidazole of the formula II

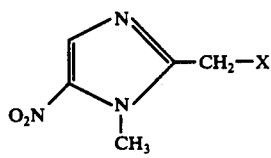

(II)

in which X stands for a halogen atom, such as fluorine, chlorine, bromine or iodine atom, or for an acyloxy group, such as an acetoxy, propionyloxy, butyryloxy, benzoyloxy, toloyloxy, nitrobenzoyloxy group, or for an arylsulfonyloxy group, such as a benzene-sulfonyloxy, toluenesulfonyloxy, or nitrobenzene-sulfonyloxy group, with a phenol or an alkali metal or ammonium salt thereof, which corresponds to the formula III

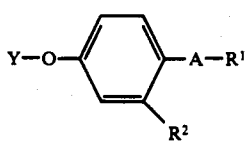

(III)

in which Y stands for a hydrogen atom, an alkali metal ion, especially a sodium or potassium ion, or ammonium, and A, $R^1$ and $R^2$ are defined as above, or
b. alkylating a nitro-imidazole of the formula IV

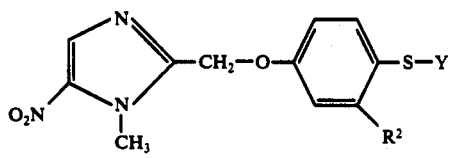

(IV)

in which Y and $R^2$ are defined as above, and optionally oxidizing the so-obtained sulfide compound of formula I to yield a sulfoxide.

As starting compounds of formula II, there may be used, for example, 1-methyl-2-chloro-methyl-5-nitro-imidazole, 1-methyl-2-bromo-methyl-5-nitro-imidazole, 1-methyl-2-iodo-methyl-5-nitro-imidazole, 1-methyl-2-acetoxy-methyl-5-nitro-imidazole, 1-methyl-2-benzoyloxy-methyl-5-nitro-imidazole, 1-methyl-2-(4-nitrobenzoyloxy)-methyl-5-nitro-imidazole or 1-methyl-2-(toluene-sulfonyloxy)-methyl- 5-nitro-imidazole.

These starting compounds of formula II may be prepared according to German Offenlegungsschrift No. 1,595,929 by reacting 1-methyl-2-hydroxymethyl-5-nitro-imidazole (cf. German Offenlegungsschrift No. 1,470,102) with a thionyl halide, or by reacting it with an acetyl, benzoyl, 4-nitrobenzoyl or 4-toluene-sulfonyl halide or anhydride.

As starting compounds of formula III, there may be used, for example, 4-methyl-mercapto-phenol, 4-ethyl-mercapto-phenol, 4-methyl-sulfinyl-phenol, 4-ethyl-sulfinyl-phenol, 3-methyl-, 3-fluoro-, 3-chloro-, 3-bromo-, 3-iodo-4-methyl-,-4-ethyl-mercapto-phenol, 3-methyl-, 3-fluoro-, 3-chloro-, 3-bromo-, 3-iodo-4-methyl- or -4-ethyl-sulfinyl phenol.

Instead of the free phenols, the alkali metal or ammonium salts thereof may also be used.

The starting compounds of formula III may be prepared by reacting 4-mercapto-phenol corresponding substituted in 3-position with one molar equivalent of a dialkyl sulfate in the presence of one molar equivalent of an alkaline substance, a dialkyl sulfate used being dimethyl or diethyl sulfate.

The alkyl-sulfinyl-phenols are prepared by reacting an alkyl-mercapto-phenol with a molar equivalent of an oxidizing agent, for example hydrogen peroxide or a peroxo acid, for example peracetic acid, perbenzoic acid, or m-chloroperbenzoic acid, as well as nitric acid or chromic acid.

As starting material of formula IV, there are mentioned 1-methyl-2-(4-mercaptophenyl-oxymethyl)-5-nitro-imidazole, 1-methyl-2-(3-methyl-4-mercaptophenyl-oxymethyl)-5-nitro-imidazole, 1-methyl- 2-(3-fluoro-4-mercaptophenyl-oxymethyl)-5-nitro-imidazole, 1-methyl-2-(3-chloro-4-mercaptophenyl-oxymethyl)-5-nitro-imidazole, 1-methyl-2-(3-bromo-4-mercaptophenyl-oxymethyl)-5-nitro-imidazole, 1-methyl-2-(3-iodo-4-mercaptophenyl-oxymethyl)-5-nitro-imidazole, or an alkali metal salt thereof. Since the mercapto compounds easily oxidize in the air to yield disulfides, their isolation is avoided and, instead, the mercapto compound in question is alkylated in statu nascendi to yield the end product of formula I.

This compound is obtained by hydrolysis of the corresponding 1-methyl-2-(4-thiocyanatophenyl-oxymethyl)-5-nitro-imidazole with concentrated sulfuric acid at room temperature under a nitrogen atmosphere in the presence of an alkylating agent, for example dimethyl sulfate. 1-Methyl-2-(4-thiocyanatophenyl-oxymethyl)-5-nitro-imidazole (m.p. 140° C) and the $R^2$-substituted products thereof are obtained by reacting a compound of formula II with 4-thiocyanato-phenol.

Methods (a) and (b) of the process of the invention are advantageously carried out using equimolar amounts of the starting compounds used, advantageously in a solvent or dispersing agent in the case of (a).

Method (b) of this process may also be carried out in the absence of such a solvent or dispersing agent. In this case, the alkylating agent used as a reaction component in excess serves as the reaction medium.

For the reactions according to method (a), polar solvents are preferably used, for example alcohols, such as methanol, ethanol, propanol, isopropanol, butanol, 2-methoxy-ethanol, 2-ethoxy-ethanol; ketones, such as acetone, diethyl-ketone, methylethyl-ketone, methylisobutyl-ketone; amides, such as dimethyl-formamide, dimethylacetamide, N-methyl-pyrrolidone, tetramethylurea, hexamethyl-phosphoric acid triamide, dimethyl-sulfoxide; heterocyclic bases, such as pyridine, picoline or quinoline.

When the free phenols of formula III are used, it is advantageous to use an acid scavenger, for example a base, such as triethylamine or pyridine, and alkali metal or alkaline earth metal carbonates and bicarbonates, hydroxides and alkoxides, for example methoxide, ethoxide or butoxide.

The reaction temperature suitable for method (a) ranges from 0° to 80° C, but advantageously it is room temperature. The reaction time ranges from a few minutes to several hours.

The alkylation reaction temperature for method (b) ranges from 20° to 80° C, preferably from 20° to 60° C. The reaction time ranges from 4 to 18 hours.

As alkalyting agents, there are used, for example, methyl or ethyl halides, especially the iodides; dimethyl or diethyl sulfate; and arylsulfonic acid esters, especially 4-toluene-sulfonic acid methyl or ethyl ester.

The sulfides of formula I (A = —S—), obtained according to the said methods (a) and (b), may be converted by oxidation into the corresponding sulfoxides (A=—SO—). The oxidation reaction is suitably carried out using one molar equivalent of an oxidizing agent, for example hydrogen peroxide or a peroxo acid, such as peracetic acid, perbenzoic acid, m-chloroperbenzoic acid, as well as nitric acid or chromic acid. The oxidation temperature generally ranges from 0° to 30 ° C.

The products of the invention are isolated according to the usual methods by distillation of the solvent used or dilution of the reaction solution with water, optionally followed by a purification by recrystallization from a suitable solvent or mixture of solvents.

The new 1-methyl-2-(phenyl-oxymethyl)-5-nitro-imidazoles of formula I according to the invention are suitable for the treatment of protozoal diseases in humans and animals are caused, for example by infections with *Trichomonas vaginalis* and *Entamoeba histolytica*. Moreover, they are effective against bacteria and fungi.

The new compounds of the invention may be administered by the oral or local route. The oral administration is generally made in the form of tablets or capsules containing, per daily dosage unit, from about 10 to 750 mg of the active ingredient, in admixture with a conventional diluent and/or exipient. Depending on the case, the individual dosage unit ranges from 2 to 100 mg of active substance per kg of body weight of the patient. For local administration, gels, creams, ointments or suppositories may be used. The following Examples illustrate the invention.

EXAMPLE 1: (Method a)

1. 1: 1-Methyl-2-(4-methylthiophenyl-oxymethyl)-5-nitro-imidazole 13.8 Grams (0.1 mol) of a potassium carbonate powder are added to a solution of 14.0 g (0.1 mol) of 4-methylmercapto-phenol in 30 ml of dimethylformamide; then a solution of 17.6 g (0.1 mol) of 1-methyl-2-chloromethyl-5-nitro-imidazole in 40 ml of dimethylformamide is added dropwise while stirring at 25° C. The weakly exothermic reaction is kept at a maximum temperature of 35° C by cooling with ice water. Stirring of the mixture is continued for 1 hour at 25° C, the reaction mixture is poured onto ice/water, the precipitate is suction-filtered, washed with water and recrystallized from methanol with an addition of charcoal.

In this manner, 19.5 g (70% of the theoretical yield) of 1-methyl-2-(4-methylthiophenyl-oxymethyl)-5-nitro-imidazole are obtained as light-yellow crystals, melting point: 116° C.

According to the process described above, the following compounds are prepared:

1.2: From 1-methyl-2-chloromethyl-5-nitro-imidazole (MCNI) and 4-ethyl-mercapto-phenol, the 1-methyl-2-(4-ethylthiophenyloxymethyl)-5-nitro-imidazole, m.p. 90° C.

1.3: 1-Methyl-2-(3-methyl-4-methylthiophenyl-oxymethyl)-5-nitro-imidazole

To a solution of 15.4 g (0.1 mol) of 3-methyl-4-methylmercaptophenol in 30 ml of dimethylformamide, 13.8 g (0.1 mol) of potassium carbonate powder are added, and then a solution of 17.6 g (0.1 mol) of 1-methyl-2-chloromethyl-5-nitro-imidazole in 40 ml of dimethylformamide is added dropwise while stirring at 25° C. The temperature of the faintly exothermal reaction is adjusted to at most 35° C by cooling with ice water. The mixture is then stirred for another hour at 25° C, poured onto ice/water, the precipitate is suction-filtered, washed with water and recrystallized from methanol with an addition of charcoal to yield 21.7 g (74% of the theoretical yield) of 1-methyl-2-(3-methyl-4-methylthiophenyl-oxymethyl)-5-nitro-imidazole in the form of yellow crystals, m.p. 108° C.

According to this method, the following compounds are prepared:

1.4: From 1-methyl-2-chloromethyl-5-nitro-imidazole (MCNI) and 3-methyl-4-ethylmercaptophenol, the 1-methyl-2-(3-methyl-4-ethylthiophenyl-oxymethyl)-5-nitro-imidazole, m.p. 80° C;

1.5: from MCNI and 3-chloro-4-methylmercaptophenol, the 1-methyl-2-(3-chloro-4-methylthiophenyl-oxymethyl)-5-nitro-imidazole, m.p. 114° C, and 1.6: from MCNI and 3-chloro-4-ethylmercaptophenol, the 1-methyl-2-(3-chloro-4-ethylthiophenyl-oxymethyl)-5-nitro-imidazole m.p. 86° C.

EXAMPLE 2: (oxidation)

2.1: 1-Methyl-2-(4-methylsulfinyl-phenyl-oxymethyl)-5-nitro-imidazole 27.9 Grams (0.1 mol) of 1-methyl-2-(4-methylthiophenyloxymethyl)-5-nitro-imidazole are dissolved in 200 ml of chloroform, and the solution is added dropwise while stirring at 25° C to a solution of 17.25 g (0.1 mol) of m-chloroperbenzoic acid in 70 ml of chloroform. The reaction mixture is stirred for 1 hour at 25° C, the solution is shaken with dilute sodium carbonate solution, the chloroform phase is separated, dried over sodium sulfate and evaporated. The residue is recrystallized from ethanol with the addition of charcoal.

Thus, 21.5 g (73% of the theoretical yield) of 1-methyl-2-(4-methyl-sulfinylphenyl-oxymethyl)-5-nitro-imidazole are obtained as yellowish crystals, m.p. 130° C.

According to the method described above, the following compound is prepared:

2.2: From 1-methyl-2-(4-ethylthiophenyl-oxymethyl)-5-nitro-imidazole, the 1-methyl-2-(4-ethylsulfinylphenyl-oxymethyl)-5-nitro-imidazole, m.p. 103° C.

2.3: 1-Methyl-2-(3-methyl-4-methylsulfinylphenyl-oxymethyl)-5-nitro-imidazole 29.3 g (0.1 mol) of 1-methyl-2-(3-methyl-4-methylthiophenyloxymethyl)-5-nitro-imidazole are dissolved in 200 ml of chloroform, and the solution is added dropwise while stirring at 25° C to a solution of 17.25 g (0.1 mol) of 3-chloroperbenzoic acid in 70 ml of chloroform. The reaction mixture is stirred for 1 hour at 25° C, shaken with dilute sodium carbonate solution, the chloroform phase is separated, dried over sodium sulfate and concentrated by evaporation. The residue is recrystallized from ethanol with an addition of charcoal, to yield 21.0 g (68% of the theoretical yield) of 1-methyl-2-(3-methyl-4-methylsulfinylphenyl-oxymethyl)-5-nitro-imidazole in the form of yellow crystals, m.p. 121° C.

According to this method, the following compounds are prepared:

2.4: From 1-methyl-2-(3-methyl-4-ethylthiophenyl-oxymethyl)-5-nitro-imidazole, the 1-methyl-2-(3-methyl-4-ethylsulfinylphenyl-oxymethyl)-5-nitro-imidazole;

2.5: from 1-methyl-2-(3-chloro-4-methylthiophenyl-oxymethyl)-5-nitro-imidazole, the 1-methyl-2-(3-chloro-4-methylsulfinylphenyl-oxymethyl)-5-nitro-imidazole, and 2.6: from 1-methyl-2-(3-chloro-4-ethylthiophenyl-oxymethyl)-5-nitro-imidazole, the 1-methyl-2-(3-chloro-4-ethylsulfinylphenyl-oxymethyl)-5-nitro-imidazole.

EXAMPLE 3: (Method b)

3.1: 1-Methyl-2-(4-methylthiophenyl-oxymethyl)-5-nitro-imidazole 5.8 g (0.02 mols) of 1-methyl-2-(4-thiocyanatophenyloxymethyl)-5-nitro-imidazole are introduced portionwise while stirring, under a nitrogen atmosphere, at room temperature, into a mixture of 26.5 ml of concentrated sulfuric acid and 5.0 g (0.04 mol) of dimethylsulfate and allowed to stand overnight at room temperature. The solution is then heated to 60° C for 30 minutes, cooled and poured onto ice/water. The precipiate is suction-filtered and washed with water. In addition to bis-4,4'-(1-methyl-5-nitro-imidazolyl-2-methoxy)-diphenyl disulfide (m.p. 160° C), column chromatographical purification on silica gel yields the 1-methyl-2-(4-methylthiophenyl-oxymethyl)-5-nitro-imidazole, m.p. 116° C.

We claim:

1. A 1-methyl-2-(phenyl-oxymethyl)-5-nitro-imidazole of the formula I

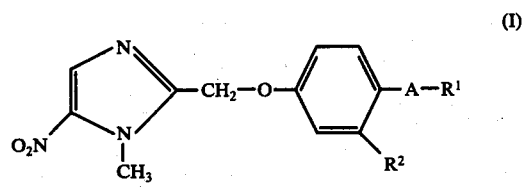

in which A stands for a sulfur atom or a sulfoxide (—SO—) group, R¹ stands for methyl or ethyl, and R² for hydrogen methyl or halogen.

2. A pharmaceutical composition suitable for treating protozoal diseases as well as diseases caused by bacteria and fungi, containing an effective amount of a compound as claimed in claim 1, in admixture or conjunction with a pharmaceutically acceptable carrier and/or excipient.

3. A method of treating protozoal diseases as well as diseases caused by bacteria and fungi, by administering to the infected organism and effective amount of a compound as claimed in claim 1.

* * * * *